United States Patent [19]
Kikuchi

[11] Patent Number: 5,008,942
[45] Date of Patent: Apr. 16, 1991

[54] DIAGNOSTIC VOICE INSTRUCTING APPARATUS

[75] Inventor: Hiromi Kikuchi, Utsunomiya, Japan

[73] Assignee: Kabushiki Kaisha Toshiba, Kawasaki, Japan

[21] Appl. No.: 277,865

[22] Filed: Nov. 30, 1988

[30] Foreign Application Priority Data

Dec. 4, 1987 [JP] Japan ................................ 62-307015

[51] Int. Cl.$^5$ .......................... G10L 5/02; A61B 5/00; G11B 31/00; G09B 5/00
[52] U.S. Cl. ........................................ 381/51; 360/80; 434/307; 128/746
[58] Field of Search .................................... 381/51–53, 381/29, 36; 434/307; 128/746; 360/79, 80

[56] References Cited

U.S. PATENT DOCUMENTS

| | | | |
|---|---|---|---|
| 3,880,144 | 4/1975 | Coursin et al. | 128/746 |
| 3,892,227 | 7/1975 | Coursin et al. | 128/746 |
| 4,012,848 | 3/1977 | Diament et al. | 434/307 |
| 4,368,988 | 1/1983 | Tahara et al. | 381/51 |
| 4,389,541 | 6/1983 | Nakano et al. | 381/51 |
| 4,420,813 | 12/1983 | Inoue et al. | 381/51 |
| 4,452,518 | 6/1984 | DiGianfilippo et al. | 360/80 |
| 4,613,944 | 9/1986 | Hashimoto et al. | 381/51 |
| 4,700,322 | 10/1987 | Benbassat et al. | 381/51 |

Primary Examiner—Dale M. Shaw
Assistant Examiner—David D. Knepper
Attorney, Agent, or Firm—Cushman, Darby & Cushman

[57] ABSTRACT

A diagnostic voice instructing apparatus has a recording/playback device including a voice recording/playback LSI and a RAM, and converts an arbitrary instruction voice to a patient, which has been input through a microphone by a user for use in a scanning operation, into a digital signal and stores the signal in corresponding one of 15 channels of the RAM, the instructing voice may be input in an arbitrary language, dialect or expression. The recording/playback device is coupled to a scan controller, which controls the scanning operation of a CT apparatus, and a host controller, which sends commands to the recording/playback device and scan controller and receives control data from the scan controller. The host controller permits an operator to prepare ID data to each patient, which includes the name, and condition, of the patient, as well as designation of the necessary instructing voice to the patient in terms of a channel quantity. When the patient ID data is read out from the host controller and supplied to the recording/playback device, and when the CT apparatus starts scanning the patient in response to a command from the scan controller, an instructing voice is read out from the channel designated by the patient ID data at the proper timing in synchronism with the scanning operation and is supplied through an amplifier to a speaker for its reproduction.

10 Claims, 2 Drawing Sheets

DIAGNOSTIC VOICE INSTRUCTING APPARATUS

BACKGROUND OF THE INVENTION

1. Field of the Invention

The present invention relates to a diagnostic voice instructing apparatus which gives instruction data to a patient in voice form in synchronism with a scanning operation at a time the patient is scanned using an X-ray computed tomography (CT) apparatus.

2. Description of the Related Art

In an X-ray CT apparatus serving as one of medical diagnostic apparatuses, image data of a patient required for medical diagnosis is acquired through scanning of the patient. In this case, however, a doctor needs to give the proper instructions to the patient in voice form at the beginning and the end of the scanning operation, or at the time of a probable interruption of the operation. To attain image data of only a single slice, the doctor has only to voice the necessary instructions, and would probably do so as it is not troublesome. To attain three-dimensional image data which requires several dozens of slices, however, the doctor's voice may become hoarse if the doctor repeatedly voices such instructions for all the slices.

As a solution to this problem, a diagnostic voice instructing apparatus, or so-called voice and scan system, has been developed which, in place of an operator, generates instructing voices that are to be given to a patient when a CT apparatus scans the patient, in synchronism with the scanning operation.

However, conventional diagnostic voice instructing apparatuses have a simple function to read out instructing voices which have been recorded in advance in a ROM or the like by a manufacture before factory shipment, in a predetermined sequence, in synchronism with the scanning operation, and they are therefore not designed for general purpose. For instance, the conventional apparatuses cannot be applied to patients who cannot understand the pre-recorded voice instructions, such as foreigners, or people whose official language is the same as that of the voice instructions but who speak and understand only dialects. Further, the contents of voice instructions or the sequence of reading out the voice instructions may vary depending on the contents of diagnosis, and the conventional diagnostic voice instructing apparatuses cannot deal with such a case.

SUMMARY OF THE INVENTION

Accordingly, it is an object of this invention to provide a general-purpose diagnostic voice instructing apparatus.

It is another object of this invention to provide a diagnostic voice instructing apparatus which can generate voice instructions in different languages, dialects and/or expressions.

It is a further object of this invention to provide a diagnostic voice instructing apparatus which can permit doctors or operators to freely alter voice instructions that have been recorded in advance.

According to one aspect of this invention, there is provided a diagnostic voice instructing apparatus which has means for recording plural types of voice instructions for the same instruction to a patient, means for specifying one of the plural types of voice instructions to be used on a patient by patient basis, and means for reproducing the specified type of voice instructions from the recording means in synchronism with an operation of a diagnosis apparatus.

BRIEF DESCRIPTION OF THE DRAWINGS

A preferred embodiment of this invention will be described below with reference to the accompanying drawings in which.

DETAILED DESCRIPTION OF THE PREFERRED EMBODIMENTS

Figure 1:
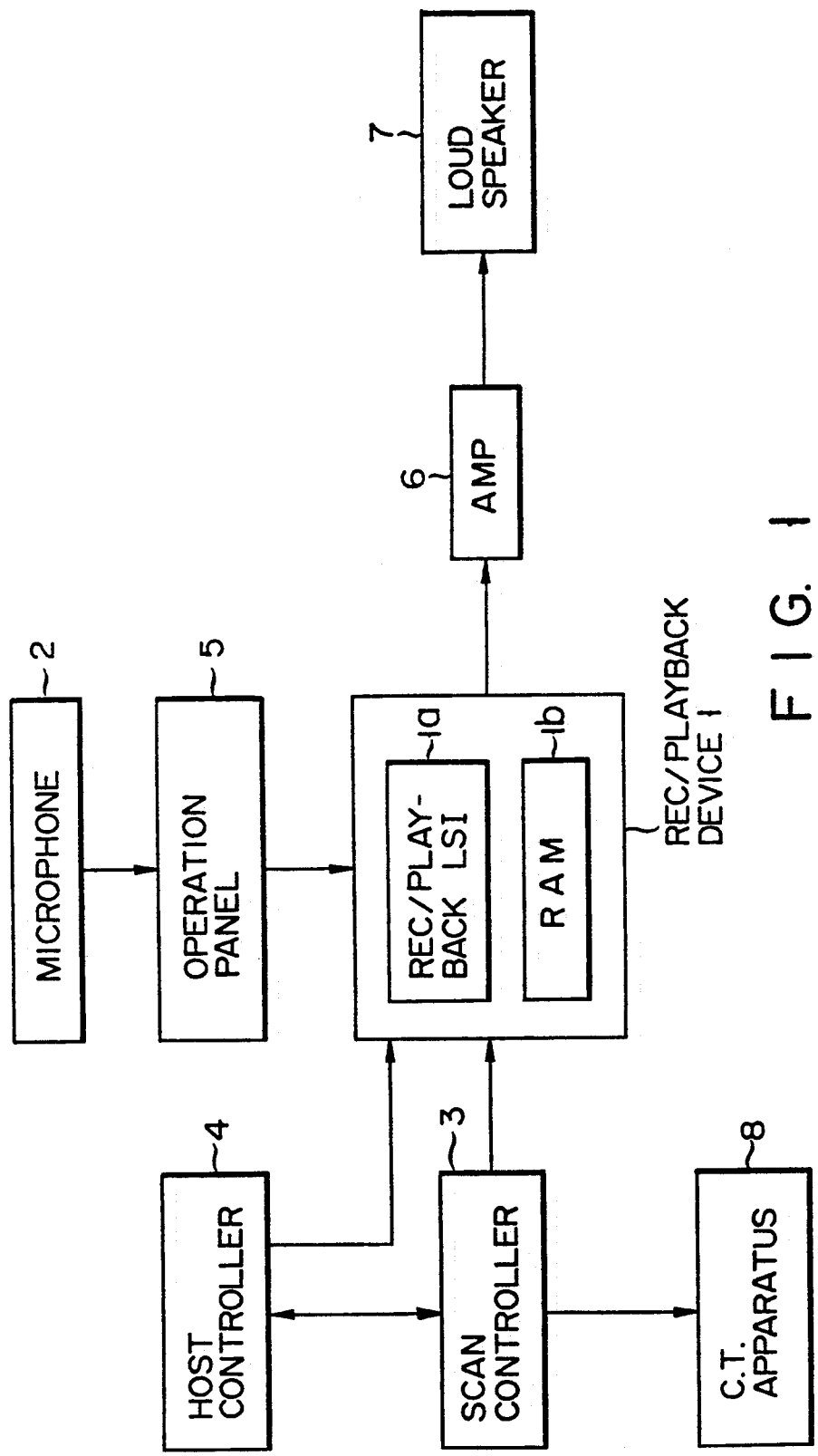
FIG. 1 is a block diagram illustrating a diagnostic voice instructing apparatus according to one embodiment of this invention.

As shown in FIG. 1, the diagnostic voice instructing apparatus according to one embodiment of this invention has a recording/playback device 1, which may be a normal analog tape recorder but is preferably of a type that can permit a high speed access to recorded voices. In this embodiment, recording/playback device 1 comprises a voice recording/playback LSI (large scale integrated circuit) 1a and a non-volatile or battery-backup type RAM (random access memory) 1b coupled to LSI 1a, although it may be a random access magnetic recording device such as a DAT or rewritable compact disk. LSI 1a converts an arbitrary instruction voice to a patient, which has been input through a microphone 2 by a user for use in a scanning operation, into a digital signal and stores the signal in RAM 1b; the instructing voice may be input in an arbitrary language, dialect or expression that would probably vary depending on the age of the patient, e.g., childish expression or elderly expression. In this embodiment, RAM 1b can store 15 voice instructions and has its memory area divided into subregions for the respective voice instructions; these regions will be called channels hereinafter. Since there are generally two or three voice instructions required for each scanning operation, 15 channels are considered sufficient to register all the necessary voice instructions in RAM 1b in different languages, dialects and/or expressions. At the time of factory shipment, standard voice instructions have been recorded in RAM 1b. Recording/playback device 1 is coupled to a scan controller 3, which controls the scanning operation of a CT apparatus 8, and a host controller 4, which sends commands to recording/playback device 1 and scan controller 3 and receives control data from the scan controller 3. Though not illustrated, host controller 4 has an input device and a display device and can permit an operator to prepare identification (ID) data to each patient and scan condition data in interactive mode while viewing the display screen. ID data includes the name, and condition, of the patient, as well as designation of the necessary instructing voices to the patient (in terms of a channel quantity). Scan condition data includes a tube voltage, tube current, scan speed, or slice depth, as well as designation of the necessary instructing voices in terms of a channel quantity. The instructing voices are in correspondence with the operation of the apparatus which is defined by the scan condition. The scan condition is usually input by using a program anatomical selection (PAS) switch provided at host controller 4.

Figure 2:
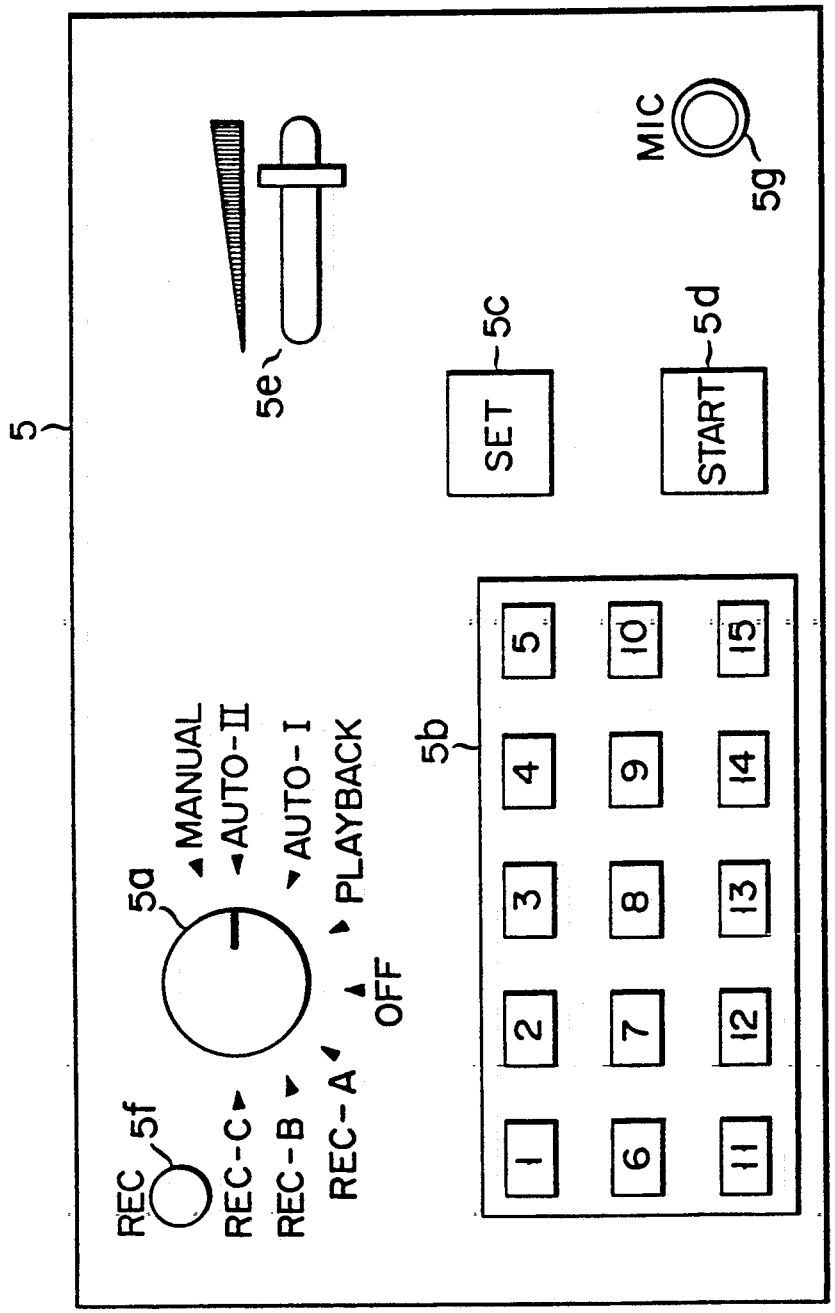
FIG. 2 is a plan view of an operation panel of the apparatus shown in FIG. 1.

FIG. 2 gives a detailed illustration of an operation panel 5 of recording/playback device 1. On panel 5 are provided mode switch 5a for switching the operation mode of recording/playback device 1, a key switch 5b for designating a memory channel through a key number from "1" to "15," a set key 5c for giving a set command to recording/playback device 1, a start key 5d for giving a start command to recording/playback device 1, a volume control knob 5e for use in playback mode, a lamp 5f that indicates a recording mode, and a microphone terminal 5g. There are several modes: REC-A to REC-C (recording), OFF, PLAY (playback), AUTO-I, AUTO-II and MANUAL. REC-A to REC-C are concerned with the sampling frequency or tone for converting an instructing voice into a digital signal, REC-A for the highest sampling frequency or tone and REC-C for the lowest one. Since the memory channel capacity for one instructing voice is constant, the recording duration will be shorter in REC-A and longer in REC-C. OFF is to stop the operation, and AUTO-I, AUTO-II and MANUAL are playback modes in which an instructing voice is reproduced automatically or manually in synchronism with the operation of CT apparatus 8. In AUTO-I and AUTO-II, the instructing voice (channel quantity and sequence) to be reproduced is determined based by host controller 4 based o the ID data and the scan condition data, respectively, and in MANUAL, it is manually set through key switch 5b. PLAY mode indicates a simple playback that is not in synchronism with the operation of CT apparatus 8 and is used for confirming of the recorded contents.

The operation of thus constituted embodiment will be described below.

To begin with, a description will be given of how to rewrite instructing voice data that has been written in advance in RAM 1b of recording/playback device 1. This operation is normally executed after a user has purchased the present apparatus but before he uses it. The user connects microphone 2 to microphone terminal 5g of operation panel 5, selects one of the recording modes (REC-A to REC-C) in accordance with the length of an instructing voice or tone using mode switch 5a, and specifies the channel to write the instructing voice using key switch 5b. Then, the user depresses start key 5d and inputs the instructing voice through microphone 2. As a result, the instructing voice is recorded into the specified channel of RAM 1b. If necessary, the above procedure is repeated for all the channels. For instance, a voice indicating a certain instruction may be recorded in channels 1 to 5 in Japanese, in channels 6 to 10 in English, and in channels 11 to 15 in German. Alternately, such a voice may be recorded in these three groups of channels respectively in childish expression, female expression and elderly expression. In this manner, different types of instructing voices desired by the user can be registered in RAM 1b.

ID data of each patient or scan condition data is prepared using host controller 4 prior to diagnosis of the patient or at the time a medical chart of the patient is prepared. At this time, the necessary instructing voices to each patient or each scan condition are designated in terms of a channel quantity, referring to the instructing voices recorded in advance in the individual channels in RAM 1b in the above-described manner. The channel quantity may be designated patient by patient, or since the types of instructions to be given are generally determined by the country, nationality, sex, age, etc. of patients, channel numbers may be determined in advance for each combination of these parameters, so that, instead of designating the channel quantity, a specific channel number can be designated by specifying the parameters for each patient.

A description will now be given of the operation of the voice instructing apparatus at the time a patient is actually scanned by CT apparatus 8, under the given conditions that many instructing voices are stored in RAM 1b of recording/playback device 1 and each patient ID data and scan condition data have been registered in host controller 4. When the AUTO-I mode and AUTO-II mode are selected using mode switch 5a, ID data and scan condition data of a patient are read out from host controller 4 and are transferred to recording/playback device 1. Channel designation data included in the patient ID data and scan condition data is written in a channel designation buffer in LSI 1a. When CT apparatus 8 starts scanning the patient in response to a command from scan controller 3, an instructing voice is read out from the designated channel in accordance with the data in the channel designation buffer at the proper timing in synchronism with the scanning operation, and is supplied through an amplifier 6 to a speaker 7 for its reproduction.

Provided that different types of instructing voices are recorded in RAM 1b in advance and these types are specified by ID data or scan condition data, therefore, it is possible to automatically generate the proper instructing voice to any patient in synchronism with the scanning operation of the CT apparatus, thus relieving the operator or doctor of the unnecessary burden.

When the MANUAL mode is selected through mode switch 5a, the read channel is not designated by patient ID data or scan condition data, so that a channel number needs to be solely designated in this case. Therefore, a channel corresponding to the first instructing voice to be reproduced is designated using key switch 5b on operation panel 5. Then, depression of set key 5c will specify that channel. Actually, the channel number is written in the channel designation buffer in LSI 1a. This procedure is repeated for the number of necessary instructing voices. When CT apparatus 8 starts scanning the patient in response to a command from scan controller 3, as in the AUTO mode, an instructing voice is read out from the designated channel in accordance with the data in the channel designation buffer at the proper timing in synchronism with the scanning operation, and is supplied through an amplifier 6 to a speaker 7 for its reproduction.

In the MANUAL mode, therefore, if the diagnosis of the present day differs from that of the other days and it is therefore necessary to reproduce an instructing voice in a channel different from the channel designated in advance for the patient ID data or scan condition data, such a requirement can be fulfilled without rewriting the patient ID data or scan condition data.

Needless to say, this invention is in no way restricted to the above particular embodiment, but can be modified in various manners within the scope and spirit of the invention. For instance, data other than instructing voices, such as a background music, may be recorded in RAM 1b, so that playing the music while scanning a patient may reduce probable nervousness of the patient. Further, not only instruction data for patients but also different types of data can be registered through a microphone in audio signal in recording/playback device 1, as well as can be reproduced therefrom, so that it is possible to provide the proper recording/playback for the user's specification. The present apparatus can be applied not only to an X-ray CT apparatus but also to other types of diagnostic apparatuses.

As described above, this invention can provide a diagnostic voice instructing apparatus which can reproduce instruction data in the proper language, dialect and/or expression for each patient in voice form in synchronism with the operation of a diagnostic apparatus, irrespective of a possible difference in country, nationality, sex and age of patients and thus can permit an operator to give the patient the proper instruction each time.

What is claimed is:

1. A voice instruction-generating apparatus for use with a medical diagnostic apparatus, the voice instruction-generating apparatus comprising:

recording means for recording plural types of voice instructions to a patient to be diagnosed, the plural types of one voice instruction having a same meaning in different types of expressions;

designating means for specifying a series of said recorded voice instructions, each instruction of the series being one of the same types of expressions; and playback means for reproducing the series of voice instructions in synchronism with an operation of said medical diagnostic apparatus.

2. The apparatus according to claim 1, wherein said expressions include different languages and dialects.

3. The apparatus according to claim 2, wherein said recording means includes means for recording a plurality of instructions of instructing voices.

4. The apparatus according to claim 3, wherein said recording means includes conversion means for sampling and converting an instructing voice into a digital signal and rewritable non-volatile memory means for storing said digital signal.

5. The apparatus according to claim 4, wherein said memory means has a plurality of areas with a given capacity each for storing a digital signal corresponding to one instructing voice, and said conversion means include means for specifying a sampling frequency, the duration of the digital signal being constant.

6. The apparatus according to claim 1, wherein said designating means includes means for preparing patient ID data having specifying data for the series of voice instructions and means for detecting the specifying data of the patient ID data.

7. The apparatus according to claim 1, wherein said designating means includes means for preparing scan condition data having specifying data for the series of voice instructions and means for detecting the specifying data of the scan condition data.

8. The apparatus according to claim 1, wherein said designating means includes key input means for designating a type of an instructing voice as a numeral.

9. The apparatus according to claim 1, wherein said diagnosis apparatus is an X-ray CT apparatus.

10. The apparatus according to claim 1, wherein said designating means includes means for respectively specifying each of the voice instructions included in the series of voice instructions.

* * * * *